United States Patent
Thomas

(10) Patent No.: US 9,292,035 B2
(45) Date of Patent: Mar. 22, 2016

(54) PACKET BASED DDS MINIMIZING MATHEMATICAL AND DAC NOISE

(71) Applicant: Andrew Thomas, Westford, MA (US)

(72) Inventor: Andrew Thomas, Westford, MA (US)

(73) Assignee: OLYMPUS SCIENTIFIC SOLUTIONS AMERICAS INC., Waltham, MA (US)

(*) Notice: Subject to any disclaimer, the term of this patent is extended or adjusted under 35 U.S.C. 154(b) by 241 days.

(21) Appl. No.: 14/163,600

(22) Filed: Jan. 24, 2014

(65) Prior Publication Data

US 2015/0212184 A1 Jul. 30, 2015

(51) Int. Cl.
*G06F 1/02* (2006.01)
*G06F 1/03* (2006.01)
*G01N 27/90* (2006.01)

(52) U.S. Cl.
CPC .......... *G06F 1/0321* (2013.01); *G01N 27/9046* (2013.01)

(58) Field of Classification Search
None
See application file for complete search history.

(56) References Cited

U.S. PATENT DOCUMENTS

| | | | | |
|---|---|---|---|---|
| 6,748,407 B1* | 6/2004 | Oga | .................. | G06F 1/0328 327/105 |
| 7,480,688 B2* | 1/2009 | Meckley | .................. | G01C 21/3611 708/271 |
| 7,844,650 B2* | 11/2010 | Warner | .................. | G06F 1/025 327/105 |
| 2009/0248772 A1* | 10/2009 | Turner | .................. | H03K 19/23 708/271 |
| 2015/0212184 A1* | 7/2015 | Thomas | .................. | G01R 35/00 702/85 |

* cited by examiner

*Primary Examiner* — David H Malzahn

(57) ABSTRACT

Disclosed are a method of and an apparatus devising a packet based DDS circuitry for performing packet based a direct digital synthesizing (DDS) function within an electronic testing instrument. The circuitry comprising a DDS logic circuit configured to execute direct digital syntheses on a plurality of consecutive packets of sine-like waves, each packet having a length of a period precisely chosen such that the sine wave at the end of one packet matches up with the sine wave at the start of the immediate subsequent packet. Also disclosed is an eddy current testing circuitry using multiple outputs of the single packet based DDS, one of the output is used in a circuit producing reference signals approximating the response signals. With the usage of the packet based DDS, the reference signal can be highly effective in nulling the unchanging portion of the response signals.

21 Claims, 7 Drawing Sheets

| Output Cycles per Packet | Ideal Packet period | Rounded Packet period | Adjusted Output Frequency | Adjusted Frequency Error | Freq OK Flag | Step Register | | |
|---|---|---|---|---|---|---|---|---|
| 1 | 11.24 | 11 | 9,090,909.09 | 2.1450% | | 390,451,572 | System Clock frequency | 100,000,000 |
| 2 | 22.47 | 22 | 9,090,909.09 | 2.1450% | | 390,451,572 | | |
| 3 | 33.71 | 34 | 8,823,529.41 | -0.8592% | | 378,967,703 | Desired output frequency | 8,900,000 |
| 4 | 44.94 | 45 | 8,888,888.89 | -0.1248% | | 381,774,871 | | |
| 5 | 56.18 | 56 | 8,928,571.43 | 0.3210% | | 383,479,223 | Frequency Tolerance | 0.05% |
| 6 | 67.42 | 67 | 8,955,223.88 | 0.6205% | | 384,623,937 | | |
| 7 | 78.65 | 79 | 8,860,759.49 | -0.4409% | | 380,566,722 | | |
| 8 | 89.89 | 90 | 8,888,888.89 | -0.1248% | | 381,774,871 | | |
| 9 | 101.12 | 101 | 8,910,891.09 | 0.1224% | | 382,719,858 | | |
| 10 | 112.36 | 112 | 8,928,571.43 | 0.3210% | | 383,479,223 | | |
| 11 | 123.60 | 124 | 8,870,967.74 | -0.3262% | | 381,005,163 | | |
| 12 | 134.83 | 135 | 8,888,888.89 | -0.1248% | | 381,774,871 | | |
| 13 | 146.07 | 146 | 8,904,109.59 | 0.0462% | OK | 382,428,595 | | |
| 14 | 157.30 | 157 | 8,917,197.45 | 0.1932% | | 382,990,714 | | |
| 15 | 168.54 | 169 | 8,875,739.64 | -0.2726% | | 381,210,115 | | |
| 16 | 179.78 | 180 | 8,888,888.89 | -0.1248% | | 381,774,871 | | |
| 17 | 191.01 | 191 | 8,900,523.56 | 0.0059% | OK | 382,274,576 | | |
| 18 | 202.25 | 202 | 8,910,891.09 | 0.1224% | | 382,719,858 | | |
| 19 | 213.48 | 213 | 8,920,187.79 | 0.2268% | | 383,119,148 | | |
| 20 | 224.72 | 225 | 8,888,888.89 | -0.1248% | | 381,774,871 | | |
| 21 | 235.96 | 236 | 8,898,305.08 | -0.0190% | OK | 382,179,263 | | |
| 22 | 247.19 | 247 | 8,906,882.59 | 0.0773% | | 382,547,694 | | |
| 23 | 258.43 | 258 | 8,914,728.68 | 0.1655% | | 382,884,681 | | |
| 24 | 269.66 | 270 | 8,888,888.89 | -0.1248% | | 381,774,871 | | |

Fig. 3a

| Output Cycles per Packet | Ideal Packet period | Rounded Packet period | Adjusted Output Frequency | Adjusted Frequency Error | Freq Flag | Step Register | | |
|---|---|---|---|---|---|---|---|---|
| 1 | 10.00 | 10 | 10,000,000.00 | 0.0000% | OK | 429,496,730 | System Clock frequency | 100,000,000 |
| 2 | 20.00 | 20 | 10,000,000.00 | 0.0000% | OK | 429,496,730 | | |
| 3 | 30.00 | 30 | 10,000,000.00 | 0.0000% | OK | 429,496,730 | Desired output frequency | 10,000,000 |
| 4 | 40.00 | 40 | 10,000,000.00 | 0.0000% | OK | 429,496,730 | | |
| 5 | 50.00 | 50 | 10,000,000.00 | 0.0000% | OK | 429,496,730 | Frequency Tolerance | 0.05% |
| 6 | 60.00 | 60 | 10,000,000.00 | 0.0000% | OK | 429,496,730 | | |
| 7 | 70.00 | 70 | 10,000,000.00 | 0.0000% | OK | 429,496,730 | | |
| 8 | 80.00 | 80 | 10,000,000.00 | 0.0000% | OK | 429,496,730 | | |
| 9 | 90.00 | 90 | 10,000,000.00 | 0.0000% | OK | 429,496,730 | | |
| 10 | 100.00 | 100 | 10,000,000.00 | 0.0000% | OK | 429,496,730 | | |
| 11 | 110.00 | 110 | 10,000,000.00 | 0.0000% | OK | 429,496,730 | | |
| 12 | 120.00 | 120 | 10,000,000.00 | 0.0000% | OK | 429,496,730 | | |
| 13 | 130.00 | 130 | 10,000,000.00 | 0.0000% | OK | 429,496,730 | | |
| 14 | 140.00 | 140 | 10,000,000.00 | 0.0000% | OK | 429,496,730 | | |
| 15 | 150.00 | 150 | 10,000,000.00 | 0.0000% | OK | 429,496,730 | | |
| 16 | 160.00 | 160 | 10,000,000.00 | 0.0000% | OK | 429,496,730 | | |
| 17 | 170.00 | 170 | 10,000,000.00 | 0.0000% | OK | 429,496,730 | | |
| 18 | 180.00 | 180 | 10,000,000.00 | 0.0000% | OK | 429,496,730 | | |
| 19 | 190.00 | 190 | 10,000,000.00 | 0.0000% | OK | 429,496,730 | | |
| 20 | 200.00 | 200 | 10,000,000.00 | 0.0000% | OK | 429,496,730 | | |
| 21 | 210.00 | 210 | 10,000,000.00 | 0.0000% | OK | 429,496,730 | | |
| 22 | 220.00 | 220 | 10,000,000.00 | 0.0000% | OK | 429,496,730 | | |
| 23 | 230.00 | 230 | 10,000,000.00 | 0.0000% | OK | 429,496,730 | | |
| 24 | 240.00 | 240 | 10,000,000.00 | 0.0000% | OK | 429,496,730 | | |

Fig. 3b

| Output Cycles per Packet | Ideal Packet period | Rounded Packet period | Adjusted Output Frequency | Adjusted Frequency Error | Freq OK Flag | Step Register | | |
|---|---|---|---|---|---|---|---|---|
| 1 | 9.09 | 9 | 11,111,111.11 | 1.0101% | | 477,218,588 | System Clock frequency | 100,000,000 |
| 2 | 18.18 | 18 | 11,111,111.11 | 1.0101% | | 477,218,588 | | |
| 3 | 27.27 | 27 | 11,111,111.11 | 1.0101% | | 477,218,588 | Desired output frequency | 11,000,000 |
| 4 | 36.36 | 36 | 11,111,111.11 | 1.0101% | | 477,218,588 | | |
| 5 | 45.45 | 45 | 11,111,111.11 | 1.0101% | | 477,218,588 | Frequency Tolerance | 0.05% |
| 6 | 54.55 | 55 | 10,909,090.91 | -0.8264% | | 468,541,887 | | |
| 7 | 63.64 | 64 | 10,937,500.00 | -0.5682% | | 469,762,048 | | |
| 8 | 72.73 | 73 | 10,958,904.11 | -0.3736% | | 470,681,348 | | |
| 9 | 81.82 | 82 | 10,975,609.76 | -0.2217% | | 471,398,850 | | |
| 10 | 90.91 | 91 | 10,989,010.99 | -0.0999% | | 471,974,428 | | |
| 11 | 100.00 | 100 | 11,000,000.00 | 0.0000% | OK | 472,446,403 | | |
| 12 | 109.09 | 109 | 11,009,174.31 | 0.0834% | | 472,840,436 | | |
| 13 | 118.18 | 118 | 11,016,949.15 | 0.1541% | | 473,174,363 | | |
| 14 | 127.27 | 127 | 11,023,622.05 | 0.2147% | | 473,460,962 | | |
| 15 | 136.36 | 136 | 11,029,411.76 | 0.2674% | | 473,709,628 | | |
| 16 | 145.45 | 145 | 11,034,482.76 | 0.3135% | | 473,927,426 | | |
| 17 | 154.55 | 155 | 10,967,741.94 | -0.2933% | | 471,060,929 | | |
| 18 | 163.64 | 164 | 10,975,609.76 | -0.2217% | | 471,398,850 | | |
| 19 | 172.73 | 173 | 10,982,658.96 | -0.1576% | | 471,701,611 | | |
| 20 | 181.82 | 182 | 10,989,010.99 | -0.0999% | | 471,974,428 | | |
| 21 | 190.91 | 191 | 10,994,764.40 | -0.0476% | OK | 472,221,535 | | |
| 22 | 200.00 | 200 | 11,000,000.00 | 0.0000% | OK | 472,446,403 | | |
| 23 | 209.09 | 209 | 11,004,784.69 | 0.0435% | OK | 472,651,903 | | |
| 24 | 218.18 | 218 | 11,009,174.31 | 0.0834% | | 472,840,436 | | |

Fig. 3c

Core Math

| Operating Frequency | Count | Step |
|---|---|---|
| 11 MHz | ~ 9 | .11 |
| 10 MHz | 10 | .1 |
| 5 MHz | 20 | .05 |
| 2 MHz | 50 | .02 |
| 1 MHz | 100 | .01 |
| 100KHz | 1000 | .001 |

410

PACKET BASED DDS MINIMIZING MATHEMATICAL AND DAC NOISE

FIELD OF INVENTION

The present invention relates generally to non-destructive testing and inspection (NDT/NDI) methods and instruments, more specifically to an improved method and circuitry for a direct digital synthesizer (DDS) with a significantly increased repeatability and a circuitry deploying such DDS in an NDT/NDI instrument, such as an eddy current instrument.

BACKGROUND OF THE INVENTION

When using an NDT/NDI device, such as an eddy current flaw detector, inspecting a test object, some instruments are designed to operate at frequencies referred to as the "operating frequency". Under most testing scenarios, the instrument sends a strong excitation signal to the probe to form the eddy current in the material under test. Since the instrument is tasked to measure very small changes to the phase and amplitude of the signal returned back to the probe as it is moved across the surface of the test object, it is highly desirable for the instrument to be able to null the unchanging portion of the signal and to better focus on the small changes. The existing eddy current instruments have not shown to be effective in nulling the unchanging portion, which largely decreases the sensitivity of the measurement and impedes the capture of very small changes or defects.

The electronic circuitry of eddy current instruments commonly involve the usage of an electronic component widely known as direct digital synthesizer (herein later as "DDS") for performing direct digital synthesizing functions. When multiple outputs of the DDS are devises for building reference signals, it can be appreciated by those skilled in the art that the high or perfectly repeatability of the DDS signals it is crucial.

It is known in the art that perfect repeatability is a property of digital signal where each and every sine wave is composed of an identical set of numbers.

A DDS of conventional architecture uses a control register to control the frequency. According to http://en.wikipedia.org/wiki/Direct_digital_synthesizer, a basic Direct Digital Synthesizer consists of a frequency reference (often a crystal or SAW oscillator), a numerically controlled oscillator (NCO) or an accumulator and a digital-to-analog converter (DAC) as shown in the figure of this reference.

The reference provides a stable time base for the system and determines the frequency accuracy of the DDS. It provides the clock to the NCO or accumulator which produces at its output a discrete-time, quantized version of the desired output waveform (often a sinusoid) whose period is controlled by the digital word contained in the frequency control register. The sampled, digital waveform is converted to an analog waveform by the DAC. The output reconstruction filter rejects the spectral replicas produced by the zero-order hold inherent in the analog conversion process.

As can be seen in the conventional DDS, the value of the frequency control register is added to the accumulator repeatedly on every system clock cycle. Thus the accumulator produces a series of ascending values. After a period of time the accumulator overflows, the carry bit is generated but it is not used. This causes the accumulator value to drop to a lower value and continues to accumulate without end. This is called modular arithmetic. The accumulator value is then passed to a circuit that performs the function SIN (accumulator*constant) to convert the accumulator values into a continuous sine wave for the digital to analog converter.

For example, a conventional DDS constructed using a 32 bit accumulator and a 100 MHz system clock can synthesize signals as low as 0.023283064 Hz. All possible operating frequencies of this DDS are integer multiples of 0.023283064 Hz. That is to say operating frequency=0.023283064*frequency control register. This provides frequency accuracy of 0.12% or better for all frequencies greater than 10 Hz.

According to Applicant's observation, signals of many frequencies produce numeric number sequences that are passed to the DAC that may take as long as 42.95 seconds ($2^{32}/10^8$) before they repeat. Because the DDS generates each consecutive sine wave which is numerically different, it generates a different math errors and digital to analog (D to A) errors. This can produce an undesired noise since signal may take as long as 42.95 seconds to repeat. This noise is spread across the spectrum at every integer multiple of 0.023283064 Hz up to 50 MHz. Since this error is caused at the roll-over from one sine wave to the next, it is hereinafter referred by the Applicant as "roll-over error".

It is Applicant's believe the math error and/or "roll-over error" is uniquely observed by the Applicant and a corresponding solution to the problem was not found either. Accordingly, a solution is needed to overcome the roll-over error of the conventional DDS as described above and to achieve advantages of higher repeatability and sensitivity of testing results and subsequently improved inspection productivity.

SUMMARY OF THE INVENTION

Accordingly, it is an object of the present disclosure to teach an apparatus and method that significantly eliminates the aforementioned problem of roll-over error of a direct digital synthesizer (DDS) by employing a novel packet design method of designing a packet based DDS, and applying such DDS to improve the sensitivity and accuracy of testing instruments.

It is another object of the present disclosure to provide an NDT/NDI instrument, particularly for testing small anomaly of test objects, with the capability of nulling unchanging portion of the testing signals and of focusing on the often small yet changing portion of the testing signals.

The foregoing and other objects of the invention are realized with the use of one or more reference signals designed to approximate the response signals and later to null the unchanging portion of the response signals.

The foregoing and other objects of the invention are further realized by applying multiple outputs of a packet based DDS with perfectly repeatable DDS functions to both the reference and response signals.

The foregoing and other objects of the invention are further realized by using a packet design method with which the DDS is designed to execute DDS function on packets of a sequence of one or more complete sine waves. The period of each packet is precisely chosen so that the sine wave at the end of one packet matches up with the sine wave at the start of the next packet so that the roll-over error is annihilated.

BRIEF DESCRIPTION OF DRAWINGS

FIGS. 3a, 3b and 3c are exhibitions of some exemplary selection processes for "output cycles per packet" according to according to the present disclosure.

DETAILED DESCRIPTION OF THE INVENTION

Figure 1:
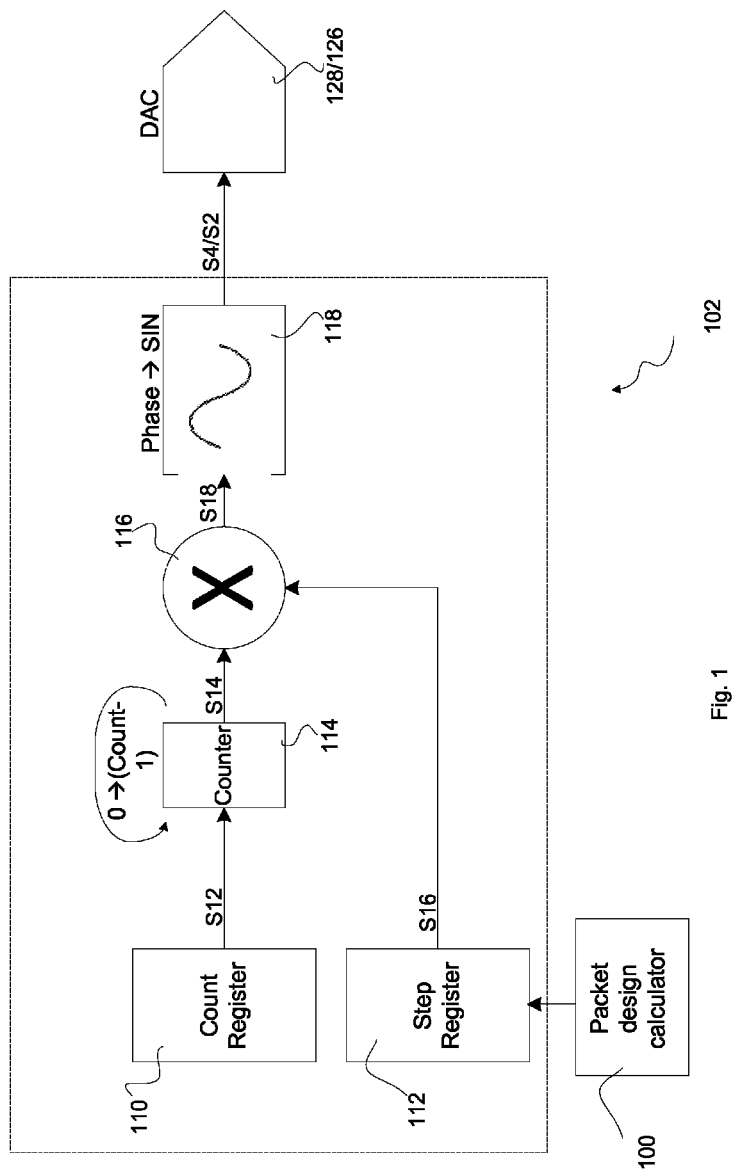
FIG. 1 is a schematic diagram of an exemplary embodiment of a Thomas DDS circuit according to the present disclosure.

Reference is made to FIG. 1, which is a schematic diagram of an exemplary embodiment of a DDS circuit according to the present disclosure.

Referring to FIG. 1, the circuit representing DDS (102) according to the present disclosure embodies a count register 110, a step register 112, and a counter 114, and a multiplier 116, and a phase-to-sine converter 18. A packet design calculator 100 is deployed either integrally with the DDS 102 or off-line, manually imported to provide selected output frequencies for all corresponding operating frequencies using a process called DDS packet design. The signal of DDS 102 or 104 is later fed to digital to analog converter 128. As depicted in FIG. 1, this DDS 102 presents a different architecture from that of the conventional ones and has been designed so that it produces consecutive sine waves from 118 that are all numerically identical. As known to those skilled in the art that many measurement instruments, including those of Eddy Current instruments, are operated at one of many predetermined operating frequencies. With this signal structure, all the errors from the math of the DDS operation and A to D converter appear at the output as stable harmonics of the operating frequency. Harmonics do not degrade the performance of the instrument. Further explanation is elaborated hereinafter.

To provide further explanation, still in reference to FIG. 1, this method can be viewed as a packet based DDS wherein a sine wave is packed into a packet of any integer number of clock periods. The concept of "packet" is herein referred to a packet of sine waves that one complete cycle of counter 114 generates. This packet is transmitted repeatedly so as to produce a continuous sine wave of the operating frequency. All math and A to D errors are repeated at exactly a packet frequency making all the energy in these errors fall on the harmonics of the packet frequency. Because the packet size is limited to a selection of time periods that is an integer number of system clock periods, it is not possible to synthesize all the required frequencies with the required precision with only one sine wave in the packet. The concept of "system clock" is known by those skilled in the art, which in this context refers to the clock of the DDS device. Usually, this system clock could be the same one as the system clock used by the processor or GPU of the instrument. This is a problem that occurs at many operating frequencies above 100 KHz. This is because a packet containing a single sine wave has a period less than 1000 system clock cycles. This reduces the resolution of frequency control. At higher frequencies many sine waves must be packaged into a single packet. Because the packet frequency remains above 100 KHz and all the noise is distributed to the harmonics of the packet frequency they do not degrade instrument performance. Herein the packet frequency is the number of packets sent each second during the DDS operation.

Continuing with reference made to FIG. 1, Count Register 110 is set by the instrument to the packet period minus 1. Count Register output signal S12 which controls the modulus of counter 114. Counter 114 increments by one on each system clock cycle. The Counter output signal S14 is an ascending sequence of numbers starting at 0 until Counter=Count Register, then the on the subsequent system clock cycle, Counter 114 is reset to zero, then repeats the sequence again indefinitely. One perfectly complete cycle of counter 114 generates a single packet.

$$\text{The counter count period} = (\text{Count Register}+1) \text{ system clock cycles} \qquad \text{Eq. 1}$$

The principle used for this improved method of designing a DDS is that a sequence of one or more complete sine waves must be generated to form each packet. The period of this sine wave or group of sine waves must closely match the packet size or period so that the sine wave at the end of one packet matches up with the sine wave at the start of the next packet. Because this is a digital system for which the only time reference is based on a system clock, therefor the output must advances in discreet phase angle steps. "System clock" and the associated "system clock frequency" are known and understood by those skilled in the art.

$$\text{Step angle} = (\text{operating frequency}/\text{system clock frequency})*2*\pi \qquad \text{Eq. 2}$$

Step Register 112 is controlled by the instrument to control the sine wave period.

Continuing making reference to FIG. 1, in an exemplary implementation according to the present disclosure, a 32 bit register is used as Step Register 112. A 32 bit register can be set to any value between 0 and 4,294,967,295. The register is needed to represent step values that are all less than 0.12 so the following significance is applied to Step Register 112. Therefore in this case, $$\text{Step angle} = (\text{Step Register}/4,294,967,296))*2*\pi \qquad \text{Eq. 3}$$

Step Register 112 is designed as follows.

$$\text{Step Register} = (2^{32}*\text{Operating frequency}/\text{system clock frequency}) \qquad \text{Eq. 4}$$

Counter output S14 is multiplied with the result from Step Register S16 by multiplier 116 resulting signal S18. S18 is a 32 bit digital signal representing the phase of the output with numeric amplitude of 0 to 4,294,967,295. If more than one sine wave is contained in each packet, then the result of multiplying S14*S16 will sometimes exceed 4,294,967,295, the bits that cannot be represented by the 32 bits of S18 are dropped or negated.

As a result, S18 is the current output phase angle.

$$\text{Phase } S18 = (2*\pi)/4,294,967,296 \qquad \text{Eq. 5}$$

As can be seen in FIG. 1, phase-to-sine wave conversion is done by a SIN(x) function inside block 118.

Output of sine function block 118 or DAC's input S4 is therefore expresses as:

$$S4 = \text{SIN}((S18\ 2*\pi)/4,294,967,296)*\text{Amplitude-Set} \qquad \text{Eq. 6}$$

Amplitude-Set sets the amplitude of the sine wave output.

Alternatively, in another example, when a 16 bit DAC is used, Amplitude-Set value range is 0 to 32,767.

Subsequently, DAC 128 or 126 converts the sine converter output S4 into an analog output.

It should be noted that the hardware or circuitry architecture shown in FIG. 1 is not the only architecture or embodiment that could be used to generate the signals described above. The most important novel aspect of the present disclosure, however, is the used of newly designed packet based DDS and the associated method of selecting a packet frequency, or the number of cycles per packet for each desired DDS output frequency, so that the circuit can synthesize the required operating frequency without the roll-over errors. As can be seen, the circuitry shown in the DDS cannot synthesize all the required output frequencies without frequency error. Therefore, many frequency possibilities must be replaced with a suitable substitute, which is a selected packet frequency. The operating principle of packet design calculator 100 for selecting the substitute frequency and packet length is herein described with the help of making reference to FIG. 2.

Alternatively, instead of using circuitry 102 of FIG. 1, this principal of the packet based DDS and the associated method herein disclosed can be deployed by providing the output of packet design calculator 100 to an arbitrary function generator known to those skilled in the art. This can achieve the same result as the circuitry shown in FIG. 1.

The process of herein described selecting substitute or suitable output frequency which should be or a close match of the respective operating frequency involves the usage of a computing tool, such as that can be devised by a spreadsheet program. The computing tool is herein referred as "packet design calculator" (100 as in FIG. 1). The purpose of using such packet design calculator is to provide a corresponding packet frequency for the DDS for each corresponding DDS output frequency or operating frequency. A table of selected packet frequencies with their corresponding DDS output frequencies is therefore generated and then imported or loaded to a memory device which is usually the memory device of the CPU or the processor of the instrument. It should be noted that at any given time during the operation of the newly designed DDS device, only one pair of the selected packet frequency with its corresponding DDS output frequency is loaded. By design, therefore operates without the "roll-over error.

Figure 2:
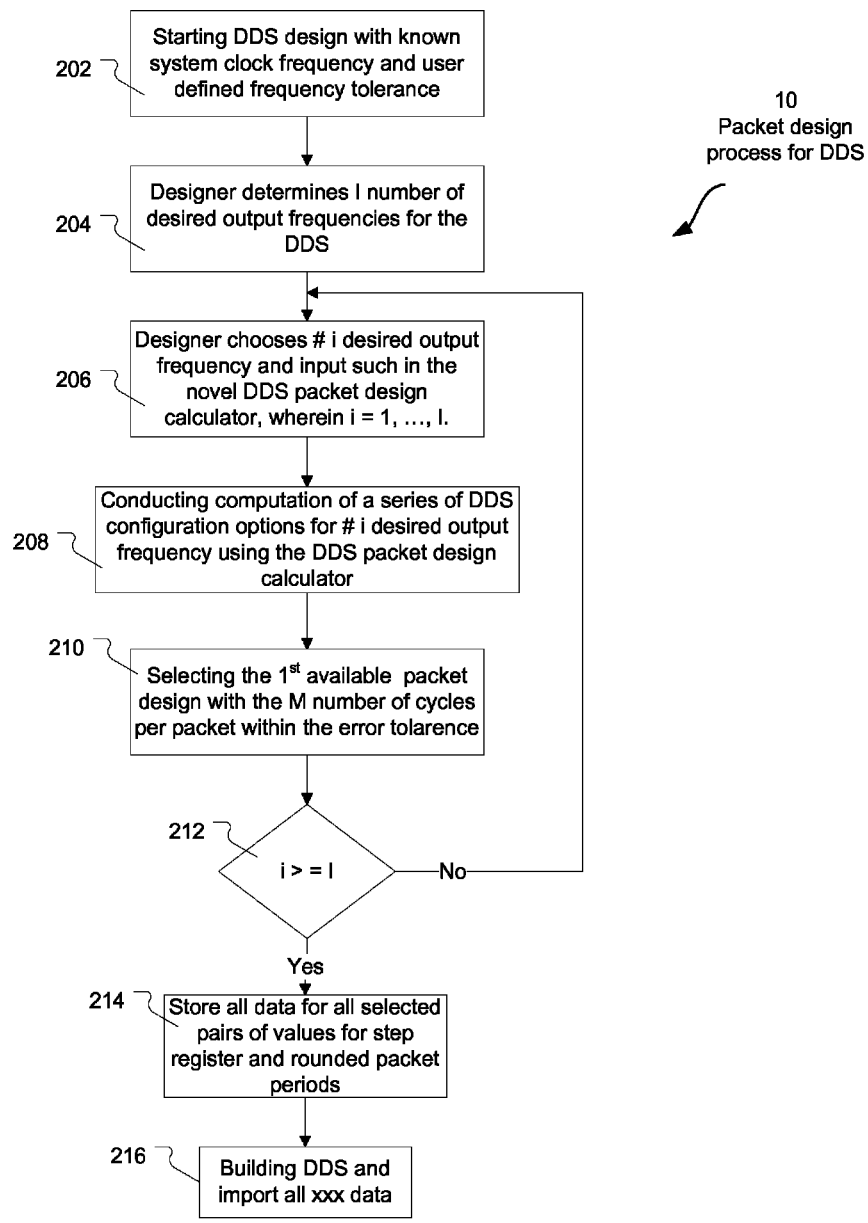
FIG. 2 is a flow chart exhibiting the process of a DDS packet design method according to the present disclosure.

Reference is now made to FIG. 2, a process shown in flow-chart steps describing the packet design method. It should be noted that the steps of this design method can be executed either by designer manually off-line, or by a data processor or a computing device residing on-board of the instrument. The design result, which is explained above, a table of packet frequencies, is then loaded in a DDS device, such as 102 shown in FIG. 1.

With further elaboration of FIG. 2, in step 202, a designer or the data processor starts the DDS design with the known system clock frequency and a range of frequency error tolerance predetermined by the designer. These are the two known values for the parameters listed to the right-hand side of FIGS. 3a, 3b and 3c, namely as "System Clock Frequency" and "Frequency Tolerance".

Further, in step 204, the designer determines the total number of N desired output frequencies for the DDS. In this regard, for further clarification, both the quantity of number N and the value of each of N specific values of the desired output frequencies for DDS are predetermined by the designer.

In step 206, either the designer or the processor chooses # i of desired output frequency and make input of such in the packet design calculator 100 of FIG. 1, where i=1, 2, . . . , N. This is further shown in FIGS. 3a, 3b and 3c to the right-hand side as the "Desired output frequency" with a specific value.

In step 208, the DDS packet design calculator 100, embodied by the presently disclosed packet design process, is used to conduct computation of a series of DDS configuration options for the #i desired output frequency. More detailed description of the packet design calculator is provided later in association with exhibitions shown in FIGS. 3a, 3b and 3c.

In step 210, the most suitable "ideal packet period" or output frequency that falls within the frequency tolerance is selected. This would be optionally and preferably the first row of data that is marked with the OK flag in column #6 for "Freq. OK Flag" in FIGS. 3a, 3b and 3c. The selection of such output frequency provides the "Packet period" value from selected "Rounded Packet period" and "Step Register" values for use in the instrument to configure the DDS for the "Desired output frequency", which is further described in association with FIGS. 3a, 3b, and 3c.

Step Register and Rounded Packet period are pairs from the same spreadsheet line. Each of which is used as a DDS configuration for a particular frequency setting.

In step 212, it is checked if the selection process for output frequency (steps 206-210) is done for all N desired output frequencies. If not, the selection process repeats until all the desired output frequencies.

In step 214, the table of DDS operational parameter with all the pairs of step register and rounded packet period for corresponding desired output frequencies are stored; and in step 216, the table of data is imported, preferably in a memory of the instrument, to build DDS as the "core math" of the DDS. In another word, the herein built DDS operates with the selected output frequency for each desired output frequency with substantially zero roll-over error, or substantially perfect repeatability. This is how the novel aspect of the present disclosure is obtained.

Reference now is made to three spreadsheet exhibitions in FIGS. 3a, 3b and 3c, which are exemplary cases showing how packet design calculator 100 works.

Referring to FIG. 3a, an exemplary case of how the packet design calculator is used to select the value of an output frequency to operate the DDS (102 in FIG. 1) in a substantially perfectly repeatable fashion.

In order for DDS 102, or any other circuits with the same function of 102, to operate without roll-over errors, or with perfect repeatability, two operational parameters are required. The two parameters are:
 a. Col. #3, The Rounded Packet Period, which is period of the packet representing the number data points in the packet.
 b. A number referred as the value of the Step Register (See later description related to FIGS. 3a, 3b and 3c.)

The three inputs of known parameters made in steps 204 and 206 to the packet design calculator and listed to the right-hand side of the spreadsheet, are: system clock frequency, in this case to be 100 MHz; desired output frequency, to be 8.9 MHz for the case shown in FIG. 3a; and frequency tolerance which is a limit of allowed frequency variance from the desired output frequency expressed in percent. In this case, the frequency tolerance is set to be 0.05%.

After these three inputs have been entered, the spread sheet provides a list of possible DDS configurations. Each row is calculated so that each packet will contain the number of output sine waves listed in the $1^{st}$ column (Output Cycles per Packet). The returned data of our most interest is the rounded packet period and Step Register value that produces an adjusted output frequency that is as close to the Desired output frequency as possible. It should be noted that the operating frequency or the "desired output frequency" of the DDS is not used in the DDS design parameter; instead its "adjusted output frequency" which falls within the frequency tolerance is used. For the exemplary case of FIG. 3a, this is because the adjusted output frequency (8,904,109.59 Hz) provides the rounded packet period, an integer number of system clock cycles and at the same time, meets the criteria of within the acceptable frequency tolerance range. A Tolerance flag show an "OK" on each line that produces a frequency that meets the user's requirements.

It should be noted that Excel sheet is only an exemplary method to carry out the subsequent calculation. Many other calculators can be used to carry out the packet design calculation based on the principle herein disclosed.

Still referring to FIG. 3a, the other details of the packet design calculator or spreadsheet are further elaborated. It should be noted that herein referred "desired output frequency" is the same as the operating frequency as it is to design the DDS to operate at certain operating frequencies.

1$^{st}$ column, "Output Cycles Per Packet": This denotes the cycles of output sine-waves per packet. It is a list of possibilities for the number of output cycles in each packet. No formula for this column.

2$^{nd}$ column "Ideal Packet period": This denotes the ideal packet size in terms of length of time per packet, in the concept of number of system clock cycles. This is the packet period needed to produce the exact desired output frequency.

$$\text{Clocks per Packet} = (\text{Output cycles of sine-wave Per Packet}) * (\text{Ideal \# of clocks per sine-wave}) \quad \text{Eq. 7}$$

For most frequencies this is not an integer, and therefore it cannot be used by the circuit hardware.

3$^{rd}$ column: "Rounded packet period", which is the "Ideal Packet period" being rounded to the nearest integer value, since the clock cycles can only be integers.

Rounded packet period can be expressed by, if using Excel spreadsheet syntax, as:

$$\text{Round ("Ideal Packet period",0)} \quad \text{Eq. 8}$$

This value of "rounded packet period" sets the counter modulus.

If selected this value will become the "Packet period", for which, in reference to FIG. 1 the Count Register 118 is set to (Packet period −1) and for the DDS to operate at for the desired output frequency.

4$^{th}$ column: "Adjusted Output Frequency", $$\text{Adjusted Output Frequency} = \text{Output Cycles Per Packet} * \text{System Clock frequency}/\text{Rounded Packet Period} \quad \text{Eq. 9}$$

Using a Packet period that has been rounded to an integer value will cause a small change in the output frequency.

5$^{th}$ column: "Adjusted Frequency Error", the magnitude showing in percentage that the frequency will be to be adjusted caused by rounding the Packet period to an integer value.

$$\text{Adjusted Frequency Error} = \text{Adjusted Output Frequency}/\text{Desired output frequency} \quad \text{Eq. 10}$$

6$^{th}$ column "OK Flag": Marks the rows that produce a frequency within in the Frequency Tolerance, which is 0.05% in this case, in Excel syntax, it's expressed as:

$$\text{IF(ABS(Adjusted Freq Error)} <= \text{Tolerance, "OK", " ")} \quad \text{Eq. 10}$$

7$^{th}$ column "Step Reg": For the row that is selected when the adjusted frequency error falls within the range of the defined tolerance, this value would be loaded into the DDS Step Register 2012.

$$\text{Step Register} = (2^{32} * \text{Adjusted Output Frequency})/\text{System clock frequency} \quad \text{Eq. 11}$$

As a result, this provides the "Packet period" value from selected "Rounded Packet period" and "Step Register" values for use in the instrument to configure the DDS for the "Desired output frequency".

Step Register and Rounded Packet period are the pairs from the same spreadsheet line of #13 in column 1. Packet design calculator 100 has therefore yield the selected pair of values of step register and rounded packet period to be 146 and 382,428,595, respectively. By providing this pair of the value defining the DDS to operate for the system clock frequency of 100 MHz, and with desired output frequency of 8.9 MHz, the DDS will be performing with perfect repeatability.

Intuitively, the number of sine waves per packet can be derived by the number of clocks per packet divided by ideal number of clocks per sine-wave cycle.

Similarly, FIGS. 3b and 3c exhibit the same calculating steps as that shown in FIG. 3a, for two scenarios with desired output frequency 10 MHz, and 11 MHz, respectively; both of are fore system clock frequency of 100 MHz.

Figure 4:
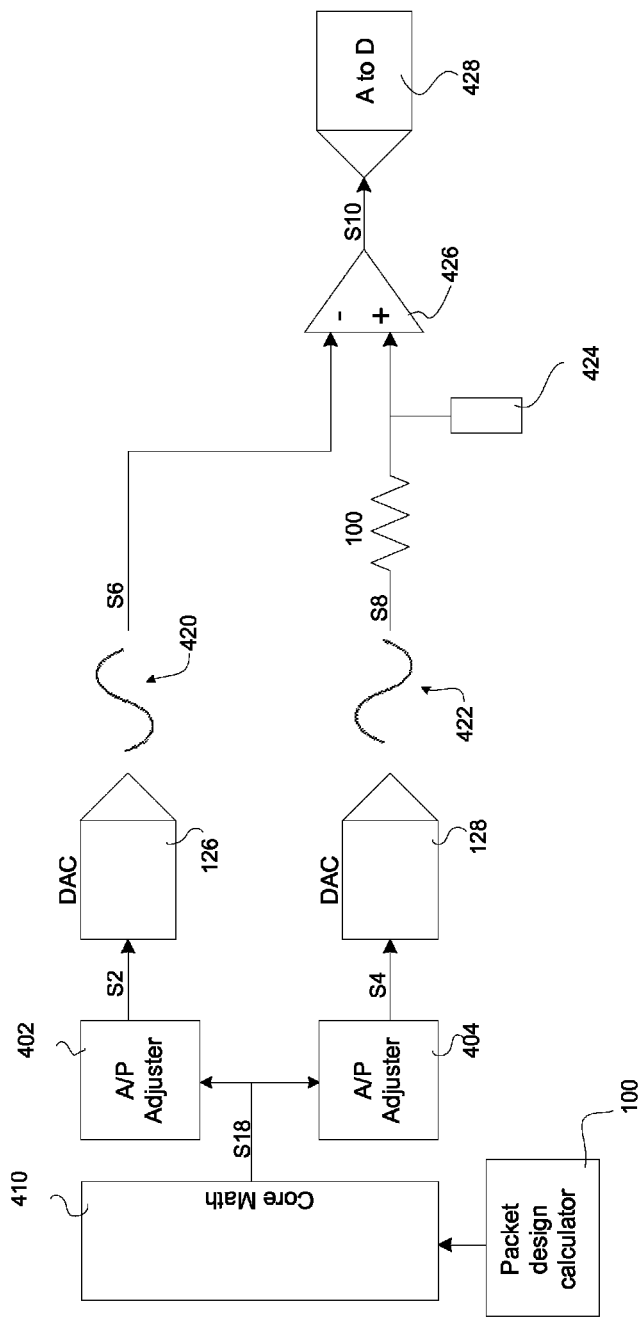
FIG. 4 is schematic diagram of an embodiment of the eddy current inspection circuitry devised with the Thomas DDS according to the present disclosure.

Reference is now made to FIG. 4, which is a schematic diagram of the analog measurement portion of the circuit of an eddy current instrument embodying the packet based DDS according to the present disclosure. As shown in FIG. 4, a DDS Core Math block 410 is the math produced by the packet based DDS 102. It can be understood the core math represents the functions executed by components 110, 112, S12, 114, S14, S16, 116 shown in FIG. 1, producing signal S18 as the output. The analog measurement portion of circuit comprises the core math block 410, a pair of amplitude-phase adjuster 402 and 404 with corresponding DAC converters 126 and 128, an amplifier 426, an A to D converter 428 and an eddy current probe 424. Preferably, a resistor 430 is also devised between the DDS logic and probe 424.

Each of amplitude-phase adjusters 402 and 404 is followed by a sine converter and further followed by a multiplier to adjust the output S2 and S4 amplitudes. Each adjuster 402 and 404 contains independent phase and amplitude registers set by the processor, such as an FPGA of the instrument. For adjuster 402, output S2=SIN(S18+102'sPhase Reg.)*102's Amplitude Reg. For adjuster 404, output S4=SIN(S18+ 102'sPhase Reg.)*104's Amplitude Reg.

Digital signals S2 and S4 are passed through DACs 126 and 128 to produce analog sine waves 420 for signal S6 and 422 for signal S8. It should be noted that S8 is the source of the probe drive signal; it is passed through a resister 430, a 100 ohm resistor in this case, to an eddy current probe 424. Signal S6 is viewed as a reference signal mirroring S8.

The voltage at the + input of amplifier 426 is preferably an attenuated and phase shifted copy of the original from signal S8. As probe 424 is moved over a testing material under test, there are small changes in the amplitude and phase at the + input to amplifier 426. Accurate measurement of these small changes in amplitude and phase is the principal of operation for an eddy current flaw detector. Signal 420 provided as input signal S6 is then adjusted to approximately equal the signal on the + input to amplifier 426. Signal S6 is subtracted from the + input signal by the differential input of amplifier 426. This greatly reduces the large unchanging portion of the probe signal so that amplifier 426 can be set to a larger gain without overloading the A to D 428. Thus the signal on S10 to the A to D contains more of the information about the material the probe is passing over and less of the unchanging probe drive signal.

It should be noted that this represents the significance and novelty of the presently disclosed design of using this "dual-DAC" design in which a nulling effect is achieved by largely reducing the "unchanged" portion of the probe signal. The two DDS channels formed by components in the upper and lower branches of circuit shown in FIG. 4 are both operating at different phase and amplitude settings. Because one DDS output is subtracted from the other, any dynamic variation in the DDS outputs would be amplified and compete with the changes caused by the probe. This would cause a reduced signal to noise ratio.

If a conventional DDS were to be used, then D to A's 126 and 128 would most likely receive none repeating sine waves with math and D to A errors that do not match; thus the errors pass through to the A to D and mix into the received signal from the probe reducing the sensitivity of the instrument. However, a perfect repeatable DDS as presently disclosed does not have this dynamic variation in the signals. There are math errors and D to A errors nonetheless. The significance is that errors are exactly the same on each and every DDS output cycle. Thus the errors are static and can be eliminated by the instruments calibration procedure. This is the significance and the key technique of the presently disclosed packet based DDS enabling the success usage of the dual DAC design achieving nulling effect of the significantly reducing the unchanging portion of the probe signal. This allows for the focus and magnifying the changing portion of the probe, which represents the anomaly that the testing is focused on.

It should be noted that two DDS logic with associated DACs can be designed with other alternative configurations with the goal of nulling or cancelling the unchanging part of the signal.

Figure 5:
FIG. 5 is an exhibition of the core math used in the Thomas DDS generated by the packet design process.

FIG. 5. Shows an exemplary portion of what core math block 410 provides to the two amplitude-phase adjusters.

Column 1 "Operating Frequency" is the same as describe previously.

Column 2 "Count" is the packet size. Because of implementation details this value is not the same as the value in Count Register 110 of FIG. 1

Column 3 "step" is the decimal format of the 112 Step register value.

Conversion formula: Decimal fraction*$2^{32}$=Binary value

As described above, the pairs of values of packet size and step are the results of the operation from the presently disclosed packet based DDS shown in FIG. 1. It should be noted that values from the core math is deployed one set at a time during operation of the measurement circuit for each specific operating frequency.

The forgoing description of embodiments associated with FIGS. 4 and 5 is illustrated as a measurement circuitry for an eddy current instrument. However, the scope and teaching of the present disclosure can be readily applied to other instruments involving signal of the nature of continuous waves. In addition, it is conceivable that, enlightened by the teaching of the present disclosure, one skilled in the art can device the packet design calculator in multiple ways either implemented by manual computation, or a digital processing module executing the herein disclosed method. The digital processing module can also be on-board the processor of the instrument or alternatively be a stand-along unit. Such alternative designs are within the scope and teaching of the present disclosure.

What is claimed is:

1. An instrument circuitry configured for performing a direct digital synthesizing (DDS) function within an electronic testing instrument, the instrument is configured to operate at a plurality of desired operating frequencies, the circuitry comprising, a DDS logic circuit configured to operate based on a basis of N number of bits and at a predetermined system clock frequency, executing direct digital syntheses on a consecutive plurality packets of sine-like waves, each packet with a length of a period containing a predetermined M number of a sequence of one or more sine-like waves, a packet design calculator determining the M number of sine-like waves of the packet and a corresponding step register value such that the sine wave at the end of one packet matches up with the sine wave at the start of the immediate subsequent packet.

2. The circuitry of claim 1, wherein the DDS logic circuit is an arbitrary function generator executing the DDS function.

3. The circuitry of claim 1, wherein the packet design calculator computes the value of step register as, Step Register=($2^N$*adjusted output frequency)/(the system clock frequency), wherein the adjusted output frequency is a value approximating one of the corresponding desired operating frequency.

4. The circuitry of claim 3, wherein the adjusted output frequency is defined as (the value of M*the system clock frequency)/(rounded packet period)), and, the rounded packet period is an integer closest to an ideal number of clock cycles per packet period which is defined as (the corresponding operating frequency/the system clock frequency), and, M=number of clocks per packet/ideal number of clocks per sine-wave cycle.

5. The circuitry of claim 1, wherein the DDS logic circuit further comprising a counter, a counter register, and a step register operated at the step register value.

6. The circuitry of claim 5, wherein the count register is predetermined by the instrument to be M minus one and the value of the count register controls the modulus of the counter, which increments by one on each of the plurality of system clock cycles.

7. The circuitry of claim 6, the output signal of the counter is an ascending sequence of numbers starting at 0 until the value of the counter equals to the value of the count register; then on the subsequent system clock cycle, the counter is reset to zero, then repeats the sequence again indefinitely.

8. The circuitry of claim 1, further including a multiplier providing the phase angle of the signals by multiplying the value of the step register with the value of the counter for each specific clock cycle.

9. The circuitry of claim 7 further comprises a phase to sine converter converting the phase to sine wave.

10. A method of designing a direct digital synthesizer (DDS) circuitry configured to operate at a plurality of operating frequencies with a plurality of corresponding desired DDS output frequencies, the DDS executing direct digital syntheses on a consecutive plurality packets of sine-like waves, each of the packets with a time-length of a period containing a predetermined M number of a sequence of one or more sine-like waves, the method comprising steps of, determining a known system clock frequency and defining a frequency error tolerance and an N number of bit as the digital basis for the DDS;

determining I number of desired output frequencies for the DDS;

choosing #i desired output frequency and input such in a DDS packet design calculator, wherein i=1, 2, . . . , I;

calculating the $M_i$ number of sine-like waves in the packet and a corresponding step register value by using an equation of, (the operating frequency/the system clock frequency) *$2^N$, repeating the steps of choosing and calculating $M_i$ until i reaches I;

designating the DDS to operate with the calculated $M_i$ for its corresponding operating frequency such that the sine-like wave at the end of one packet matches up with the sine-like wave at the start of the immediate subsequent packet.

11. The method of claim 10 further comprises of a step of employing a count register, and a counter and a step register calculating the step register value.

12. The method of claim 11, wherein the DDS circuitry operates at a plurality of system clock cycles, and the method further comprising of determining the count register to be M minus one and with the value of the count register controlling the modulus of the counter, which increments by one on each of the plurality of system clock cycles.

13. The method of claim 11, the output signal of the counter is an ascending sequence of numbers starting at 0 until the value of the counter equals to the value of the count register; then on the subsequent system clock cycle, the counter is reset to zero, then repeats the sequence again indefinitely.

14. The method of claim 13, wherein a perfectly complete cycle of the counter generates a single packet.

15. The method of claim 11 further including employing a multiplier to providing the phase angle of the signals by multiplying the value of the step register with the value of the counter for each specific clock cycle.

16. An analog measurement circuitry of an eddy current instrument configured to conduct eddy current testing on a testing object, the circuitry comprising,
a packet based direct digital synthesizer (DDS) configure to execute direct digital syntheses on a plurality of consecutive packets of sine-like waves, each packet with a length of a period containing a predetermined M number of sine-like waves, wherein the packet based DDS further comprising a packet design calculator computing the number M and a step register value so that at the end of each of the packet the sine-like wave matches up with the sine-like wave at the start of the immediate subsequent packet;
a probe interface circuit branch comprising an eddy current probe providing probe signals, and a first digital-analog converter receiving step-up signals as input and is connected to the probe, receiving drive signals and a response, wherein the probe signals including an unchanging portion and a changing portion reflecting any anomaly of the test object;
a reference circuit branch comprising at least a second phase-amplitude adjuster receiving the step-up signals as input and is connect to a corresponding second digital-analog converter,
an amplifier receiving signals from both the probe circuit branch and the reference circuit branch, wherein the at least second phase-amplitude adjuster is configured to adjust its phase and amplitude to be substantially the same as those of the probe signals, and to provide a null effect of the unchanging portion of the probe signals.

17. The measurement circuitry of claim 16, wherein the probe interface circuit branch further comprises a first phase-amplitude adjuster, which working in unison with the second phase-amplitude adjuster, adjusts the phase and amplitude of the reference circuit branch to be substantially the same as those of the probe signals.

18. The measurement circuitry of claim 16, wherein the packet design calculator computes the step register value as,
Step Register=($2^N$*adjusted output frequency)/(the system clock frequency), wherein the adjusted output frequency is a value approximating one of the corresponding desired operating frequency; and,
wherein the adjusted output frequency is defined as (the value of M*the system clock frequency)/(rounded packet period)), and,
wherein the rounded packet period is an integer closest to an ideal number of clock cycles per packet period which is defined as (the corresponding operating frequency/the system clock frequency), and,
M=number of clocks per packet/ideal number of clocks per sine-wave cycle.

19. The circuitry of claim 16 the packet based DDS further comprising a count register, and a counter and a step register using the step register value.

20. The circuitry of claim 19, wherein the packet based DDS has a system clock that has a plurality of system clock cycles, and the count register is predetermined by the instrument to be M minus one and the value of the count register controls the modulus of the counter, which increments by one on each of the plurality of system clock cycles.

21. The circuitry of claim 20, the output signal of the counter is an ascending sequence of numbers starting at 0 until the value of the counter equals to the value of the count register; then on the subsequent system clock cycle, the counter is reset to zero, then repeats the sequence again indefinitely.

* * * * *